United States Patent [19]

Sabahi et al.

[11] Patent Number: 5,536,872
[45] Date of Patent: *Jul. 16, 1996

[54] MICHAEL ADDITION PROCESS

[75] Inventors: Mahmood Sabahi; Kenneth C. Lilje, both of Baton Rouge, La.

[73] Assignee: Albemarle Corporation, Richmond, Va.

[*] Notice: The term of this patent shall not extend beyond the expiration date of Pat. No. 5,350,875.

[21] Appl. No.: 511,198

[22] Filed: Aug. 4, 1995

Related U.S. Application Data

[63] Continuation-in-part of Ser. No. 297,087, Aug. 29, 1994, abandoned.

[51] Int. Cl.$^6$ .................................................. C07C 67/00
[52] U.S. Cl. ................................. 560/204; 560/190
[58] Field of Search ...................................... 560/190, 204

[56] References Cited

U.S. PATENT DOCUMENTS

| | | | |
|---|---|---|---|
| 5,350,875 | 9/1994 | Kumar et al. | 560/190 |
| 5,430,177 | 7/1995 | Sabahi et al. | 560/190 |

*Primary Examiner*—Samuel Barts
*Attorney, Agent, or Firm*—Philip M. Pippenger

[57] ABSTRACT

The reaction between a Michael donor corresponding to the formula Z—CH(E)(E') (e.g., a dialkyl malonate) and a Michael acceptor corresponding to the formula CTT'=CT"G (e.g., an alkyl acrylate or alkyl acrylate dimer) in the presence of a solid inorganic base catalyst is expedited by simultaneously feeding the reactants through a column of the solid inorganic base catalyst at a temperature of about 25°–120° C. to form an effluent containing a product corresponding to the formula Z'—C(E)(E")$_p$—Q$_s$, in which formulas T, T', and T" are independently selected from hydrogen, G', and organic groups, with the proviso that at least one of T, T', and T" must be hydrogen; E, E", G, and G' are independently selected from —CN, —COOR, and —C(O)R' electron withdrawing groups; E' is hydrogen or a —COOR, —C(O)R', or —CN electron withdrawing group; R and R' represent alkyl or cycloalkyl groups of up to 30 carbons; Z is hydrogen or an alkyl or cycloalkyl group of up to 30 carbons; Z' is Z or —[CTT'—CT"G]$_w$—CTT'—CHT"G; Q is —[CTT'—CT"G]$_t$—CTT'—CHT"G; p is zero or one; s is respectively two or one; and each of t and w represents zero or a positive integer such that the sum of t and w in a molecule is 0–30.

8 Claims, No Drawings

5,536,872

1

MICHAEL ADDITION PROCESS

CROSS-REFERENCE TO RELATED APPLICATION

This application is a continuation-in-part of application Ser. No. 08/297,087, filed Aug. 29, 1994, now abandoned.

FIELD OF INVENTION

This invention relates to Michael addition products and, more particularly, to a novel process for preparing them.

BACKGROUND

The Michael reaction is a known process wherein a Michael acceptor is reacted with a Michael donor in the presence of a basic catalyst to elongate a carbon chain. At one time, Michael reactions were always conducted by a homogeneous basic catalysis achieved by dissolving a basic compound in a reactant or by solubilizing it with the aid of a solvent or a phase transfer catalyst—such reactions being taught, e.g., in PCT application WO 93/13188 (Sabahi), U.S. Pat. No. 5,347,043 (Sabahi et al.), and the references cited therein. Then, as disclosed in U.S. Pat. No. 5,350,875 (Kumar et al.), it was unexpectedly discovered that an undissolved basic catalyst could be used to catalyze the reactions.

The heterogeneously catalyzed processes of Kumar et al. have advantages over the previously-known Michael reactions. However, like the homogeneously catalyzed processes, they require longer reaction times than are desired in the preparation of addition products from dialkyl malonates and alkyl acrylates.

SUMMARY OF INVENTION

It has now been found that a Michael reaction can be expedited by passing the reactants through a heated column of a solid inorganic base catalyst and, if desired, recycling the effluent through the column one or more times.

Thus, the invention resides in a process which comprises simultaneously feeding a Michael donor corresponding to the formula Z—CH(E)(E') and a Michael acceptor corresponding to the formula CTT'=CT"G through a column of a solid inorganic base catalyst at a temperature of about 25°–120° C. to form a product corresponding to the formula Z'—C(E)(E")$_p$—Q$_s$, in which formulas T, T', and T" are independently selected from hydrogen, G', and organic groups, with the proviso that at least one of T, T', and T" must be hydrogen; E, E", G, and G' are independently selected from —CN, —COOR, and —C(O)R' electron withdrawing groups; E' is hydrogen or a —COOR, —C(O)R', or —CN electron withdrawing group; R and R' represent alkyl or cycloalkyl groups of up to 30 carbons; Z is hydrogen or an alkyl or cycloalkyl group of up to 30 carbons; Z' is Z or —[CTT'—CT"G]$_w$—CTT'—CHT"G; Q is —[CTT'—CT"G]$_t$—CTT'—CHT"G; p is zero or one; s is respectively two or one; and each of t and w represents zero or a positive integer such that the sum of t and w in a molecule is 0–30.

DETAILED DESCRIPTION

Michael donors and acceptors which can be used in the process of the invention include all of the Z—CH(E)(E') and CTT'=CT"G compounds generally described above —reactants which have one or more electron withdrawing groups attached to an organic group which is hydrocarbyl or at least predominantly hydrocarbyl in nature, i.e., contains only carbon and hydrogen or (2) contains carbon, hydrogen, and one or more other atoms but contains so few of the other atoms that the predominantly hydrocarbyl nature of the group is preserved.

The preferred reactants are usually compounds in which these organic groups are hydrocarbyl. However, when a reactant includes a predominantly hydrocarbyl group that contains atoms other than carbon and hydrogen, these other atoms may be part of a chain or ring as hetero atoms, such as oxygen, sulfur, or phosphorus atoms; or they may be present in substituent groups, such as alkoxy, halo, or cyano groups as long as the number of hetero atoms or non-hydrocarbyl substituents in the group is not high enough to destroy its predominantly hydrocarbyl nature.

To preserve the predominantly hydrocarbyl nature of the group, the number of hetero atoms or non-hydrocarbyl substituents therein should not exceed 0.3 per carbon and is preferably not more than 0.1 per carbon. These predominantly hydrocarbyl groups can be regarded as being virtually the same as the true hydrocarbyl groups to which they most closely correspond, so, e.g., the term alkyl, as used herein, should be understood as including the predominantly alkyl groups as well as the alkyl groups normally denoted by those terms. Exemplary of such groups are chlorohexyl, bromodecyl, ethoxyoctyl, and cyanononyl.

The Michael donor employed in the process may be a single compound or a mixture of two or more compounds having the Z—CH(E)(E') formula. When a single Michael donor is employed in the reaction, each E in the Z'—C(E)(E")$_p$—Q$_s$ product is the same, as is each E" in that product. However, when a mixture of two or more donors is used, different molecules of the product will contain different E and/or E" groups when the donors contain different E and/or E' groups.

Exemplary of utilizable donors are (1) the methyl, ethyl, propyl, isopropyl, butyl, isobutyl, t-butyl, pentyl, hexyl, chlorohexyl, heptyl, octyl, 2-ethylhexyl, decyl, bromodecyl, ethoxyoctyl, dodecyl, tetradecyl, hexadecyl, octadecyl, eicosyl, docosyl, tetracosyl, triacontyl, cyclopropyl, cyclopentyl, cyclohexyl, and cyclooctyl esters of alkanoic and substituted alkanoic acids such as acetic, cyanoacetic, propionic, and butyric acids, (2) the corresponding diesters of 1,1-dicarboxyalkanes and other dicarboxyalkanes (e.g., succinic, glutaric, and higher acids of the oxalic acid series) in which the alkane moiety is a divalent hydrocarbylene radical derived from an alkane such as methane, ethane, propane, isopropane, butane, isobutane, t-butane, penlane, hexane, heptane, octane, propoxypentane, butoxypentane, nonane, decane, or ethoxyoctane; (3) the corresponding diesters of 1,1-dicarboxy-1-cycloalkylmethanes in which the cycloalkyl substituent is cyclopropyl, cyclopentyl, cyclohexyl, or cyclooctyl; (4) the corresponding dicyano- and diacyl-substituted alkanes and cycloalkylmethanes in which the acyl groups are acetyl, propionyl, butyryl, or isobutyryl; and (5) the corresponding cyano- or acyl-substituted alkanoic and cycloalkylethanoic acid esters.

The most preferred Michael donors are usually those containing two —COOR electron withdrawing groups, especially the more reactive esters in which R is a lower alkyl group containing 1–10 carbons (usually 1–4 carbons), and most especially the dimethyl and diethyl malonates. However, other donors that are sometimes preferred are the methyl and ethyl cyanoacetates, acetoacetates, and propionylacetates; malononitrile; acetonitrile; and dipropionylmethane.

Michael acceptors which may be reacted with these donors are CTT'=CT"G compounds in which T, T', and T"

are independently selected from hydrogen, G', and organic groups, with the proviso that at least one of T, T', and T" must be hydrogen; and G and G' are electron withdrawing groups selected from the —COOR, —C(O)R', and —CN groups described above. Any organic groups represented by T, T', or T" are usually hydrocarbyl or predominantly hydrocarbyl groups, such as alkyl, alkoxyalkyl, alkylthioalkyl, cycloalkyl, dialkylaminocycloalkyl, aryl, haloaryl, alkoxyaryl, aralkyl, and alkaryl groups of up to 10 carbons. However, in one of the preferred embodiments of the invention, the acceptor is a compound in which T and T' represent hydrogen and T" is an organic group corresponding to the formula —[$CH_2$—CH(COOR")]$_m$—($CH_2$)$_n$—COOR" wherein R" is an alkyl of 1–30 carbons (most commonly 1–10, and preferably 1–4 carbons), m is zero or an integer of 1–10, and n is an integer of 1–4, with the proviso that m must be zero when n is one.

Exemplary of utilizable acceptors containing a —[$CH_2$—CH(COOR")]$_m$—($CH_2$)$_n$—COOR" group are the dialkyl itaconates and the alkyl acrylate dimers, trimers, and/or tetramers, i.e., the compounds in which n is 1 or 2 and m is 0–2—m always being 0 when n is 1.

Examples of other utilizable acceptors are (1) the methyl, ethyl, propyl, isopropyl, butyl, isobutyl, t-butyl, pentyl, hexyl, chlorohexyl, heptyl, octyl, decyl, bromodecyl, ethoxyoctyl, dodecyl, tetradecyl, hexadecyl, octadecyl, eicosyl, docosyl, tetracosyl, triacontyl, cyclopropyl, cyclopentyl, cyclohexyl, and cyclooctyl esters of acrylic, methacrylic, ethacrylic, crotonic, and cinnamic acids, (2) the corresponding esters of 1-carboxy- 1-cyanoethylene and the corresponding diesters of 1,1-dicarboxy-2-cyanoethylene and 1,1-dicarboxyethylene, and (3) nitriles such as acrylonitrile, methacrylonitrile, ethacrylonitrile, dicyanoethylene, and tricyanoethylene, as well as the corresponding compounds in which the α- or β-carbon bears an organic substituent such as a propyl, isopropyl, butyl, isobutyl, t-butyl, pentyl, hexyl, chlorohexyl, heptyl, octyl, ethylthiohexyl, decyl, bromodecyl, cyanodecyl, ethoxyoctyl, cyclopropyl, cyclopentyl, cyclohexyl, cyclooctyl, N,N-dimethylaminocyclohexyl, methylphenyl, bromophenyl, ethoxyphenyl, or benzyl group.

Of these compounds, the Michael acceptors which are apt to be most preferred are (A) those in which T, T', and T" are hydrogen and G is a —COOR, —C(O)R', or —CN group wherein R and R' are alkyls of 1–10 carbons, preferably 1–4 carbons, and more preferably methyl or ethyl and (B) the corresponding compounds in which one or two of the hydrogens represented by T, T', and T" is replaced with a G' electron withdrawing group which may be the same as G or a different group selected from —CN, —COOR, and C(O)R'. The especially preferred Michael acceptors are the methyl and ethyl acrylates, acrylonitrile, dicyanoethylene, and tricyanoethylene.

When a single Michael acceptor is employed in the reaction, each T, T', T", and G in the product is the same as each other T, T', T", and G. However, when a mixture of two or more acceptors is used and the different acceptors have different T, T', T", G, and/or G' groups in their molecules, those differences will be reflected in the product. For example, when methyl acrylate and methyl methacrylate are simultaneously or consecutively reacted with a Michael donor, each T and T' in the product molecules will represent hydrogen and each G will represent a —COOCH$_3$ group; but some of the T" groups will represent hydrogen, while the others will be methyl groups. Similarly, when methyl acrylate and acrylonitrile are simultaneously or consecutively reacted with a donor, each T, T', and T" in the product molecules will represent hydrogen; but some of the G groups will be —COOCH$_3$ while others will be —CN.

As will be readily understood, the proportions in which the reactants are mixed varies with the product desired—the acceptor/donor mol ratio in the mixture being, e.g., at least 1/1 when the product is to contain a substantial number of molecules containing three acceptor moieties and at least 2/1 when the product is to contain a substantial number of molecules containing four acceptor moieties. Most commonly, a stoichiometric excess of the acceptor is employed; and the reactants are mixed so as to provide acceptor/donor mol ratios in the range of 2-30/1, preferably 2-15/1, and more preferably 2-6/1.

The simultaneous feeding of the reactants through the column of catalyst may be accomplished by premixing the reactants in the desired proportions before introducing them into the column or by simultaneously feeding separate streams of the reactants at rates such that the reaction mixture passing through the column contains the reactants in the desired proportions. However, it is usually more convenient to premix the reactants.

The catalyst employed in the reaction is a solid inorganic base, such as an alkali or alkaline earth metal hydroxide, alkoxide, amide, or carbonate—preferably an alkali metal carbonate, and most preferably potassium carbonate. As in known reactions utilizing a column of catalyst, its columnar nature is obtained by packing it into a columnar vessel; and its being used in this manner instead of being mixed with the reactants increases the amount of catalyst contacting the donor and acceptor molecules during the reaction. As a result, the rate of reaction is considerably increased, providing high conversions of the reactants to desired products in a fraction of the time required in the conventional, batch-type reaction. Thus, e.g., conversions of 70–90% with little or no co-formation of by-product can be achieved with contact times of 1–15 minutes.

As already indicated, the column of catalyst is maintained at a temperature of about 25°–120° C. as the reactants are passed through it. The use of a jacketed vessel to hold the column of catalyst is a convenient way of maintaining the desired temperature, which is preferably in the range of about 60°–110° C.

The amount of acceptor reacted with the donor in a single pass through the column of catalyst varies, of course, with the length of the column as well as with the particular temperature, catalyst, and reactants employed—shorter columns, lower temperatures, less active catalysts, and less reactive reactants all being factors that decrease this amount. However, when it is wished to use a reactant/catalyst/reaction temperature combination that would not permit the desired product to be obtained in a single pass through a column of catalyst, it is not necessary to employ a longer catalyst column in order to provide that product. Increasing the amount of acceptor reacted with the donor can be achieved either by using .a longer catalyst column or by recycling the effluent stream one or more times. Successive passes through the column can effect conversions of close to 100% even when a relatively short column is employed.

Because of all of the other factors that can be varied to influence the amount of acceptor reacted with the donor in a single pass, and because of the fact that multiple passes through the catalyst column can be performed, the length of the catalyst column is not critical. However, it is generally preferred that the catalyst column have a length such that a single pass through the column can be accomplished in 5–60 minutes when the reaction mixture is fed at a rate of 2 mL/minute.

Like the processes of Sabahi, Sabahi et al., and Kumar et al., the process of the invention results in the formation of a mixture of compounds containing different numbers of acceptor moieties per molecule. This product may be fractionated into individual components or groups of components and/or subjected to one or more additional reactions, such as transesterification, after completion of the Michael reaction. However, the product mixtures themselves are also useful materials, so fractionations of the products are frequently unnecessary; and post-treatments of the products, e.g., by transesterification, are used only when the product of the Michael reaction does not have the properties desired for its end use but can acquire those properties by such a post-treatment.

The products of the reactions are typically washed with water to remove any unreacted materials prior to being used in their intended applications; and, if desired, they can then be subjected to fractional distillation to purify them further. However, one of the advantages of the process of the invention is that it reduces or obviates the need for such further purification.

Like the processes of Sabahi and Sabahi et al., the process of the invention is of particular value as a means of preparing ester oils having utility as lubricants, especially the ester lubricants which can be used in refrigeration compositions containing fluorocarbon refrigerants, such as R-134a. Its primary advantages over the earlier processes are its more expeditious preparation of the desired products, its ability to eliminate the need for purification steps, and its consequent lower cost.

The following examples are given to illustrate the invention and are not intended as a limitation thereof.

COMPARATIVE EXAMPLE A

Process of Kumar et al.

Charge a reaction vessel with 26.4 g (0.2 mol) of dimethyl malonate and 0.28 g (0.002 mol) of potassium carbonate, heat to 50° C., and slowly add 34.4 g (0.4 mol) of methyl acrylate over a period of 1.75 hours so as to keep the temperature below 60° C. and thus prevent polymerization of the acrylate. GC analysis of the reaction mixture at this point shows the product to consist of 86% trimethyl ester of 1,1,3-propanetricarboxylic acid and 14% tetramethyl ester of 1,3,3,5-pentanetetracarboxylic acid.

Continue heating the reaction mixture at 50° C. and periodically withdraw samples for analysis. The samples withdrawn after 3.25 hours, 5.25 hours, and 23 hours of total reaction time are shown by analysis to contain, respectively, (A) 85% triester and 15% tetraester, (B) 73% triester and 26% tetraester, and (C) 17% triester, 76% tetraester, and small amounts of heavier components.

EXAMPLE 1

Mix 26.4 g (0.2 mol) of dimethyl malonate with 34.4 g (0.4 mol) of methyl acrylate and pass the mixture once through a 4×4 cm column of anhydrous potassium carbonate at 50° C. over a period of 30 minutes. GC analysis shows the product to consist of 31% trimethyl ester of 1,1,3-propanetricarboxylic acid, 61% tetramethyl ester of 1,3,3,5-pentanetetracarboxylic acid, and 8% heavier products.

EXAMPLE 2

Mix 26.4 g (0.2 mol) of dimethyl malonate with 51.6 g (0.6 mol) of methyl acrylate and pass the mixture once through a 4×4 cm column of anhydrous potassium carbonate at 70° C. over a period of 35 minutes. GC analysis shows the product to consist of 17% trimethyl ester, 75% tetramethyl ester, 5% heavier products, and some unreacted dimethyl malonate and methyl acrylate.

Recycle the effluent and pass it through the column one more time. GC analysis shows the product to consist of 91% tetramethyl ester and 9% pentamethyl ester of 1,3,3,5,7-heptanepentacarboxylic acid.

EXAMPLE 3

Mix 26.4 g (0.2 mol) of dimethyl malonate and 64 g (0.5 mol) of butyl acrylate and pass the mixture twice through a column similar to that of Example 2. GC analyses show the product of the first pass to contain 25% triester and 68% tetraester and the product of the second pass to contain 20% triester and 76% tetraester.

EXAMPLE 4

Mix 66 g (0.5 mol) of dimethyl malonate and 141 g (1.1 mols) of butyl acrylate and pass the mixture over a period of one hour through a jacketed column packed with 50 g of anhydrous potassium carbonate and maintained at 85° C. to form a product which analysis shows to contain 12% triester, 69% tetraester, and unreacted butyl acrylate. Continue recycling the effluent through the column until the product shows a composition of 10% triester, 72% tetraester, and unreacted butyl acrylate. Then increase the column temperature to 100° C. and pass the mixture through the column one more time. Analysis shows the product to contain 5% triester, 82% tetraester, 8% heavier components, and some unreacted butyl acrylate.

We claim:

1. A process which comprises simultaneously feeding a Michael donor corresponding to the formula Z—CH(E)(E') and a Michael acceptor corresponding to the formula CTT'=CT"G through a column of a solid inorganic base catalyst at a temperature of about 25°–120° C. to form an effluent containing a product that corresponds to the formula Z'—C(E)(E")$_p$—Q$_s$, in which formulas T, T', and T" are independently selected from hydrogen, G', and organic groups, with the proviso that at least one of T, T', and T" must be hydrogen; E, E", G, and G' are independently selected from —CN, —COOR, and —C(O)R' electron withdrawing groups; E' is hydrogen or a —COOR, —C(O)R', or —CN electron withdrawing group; R and R' represent alkyl or cycloalkyl groups of up to 30 carbons; Z is hydrogen or an alkyl or cycloalkyl group of up to 30 carbons; Z' is Z or —[CTT'—CT"G]$_w$—CTT'—CHT"G; Q is —[CTT'—CT"G]$_t$—CTT'—CHT"G; p is zero or one; s is respectively two or one; and each of t and w represents zero or a positive integer such that the sum of t and w in a molecule is 0–30.

2. The process of claim 1 wherein the donor and acceptor are premixed before being fed through the catalyst column.

3. The process of claim 1 wherein separate streams of the donor and acceptor are simultaneously fed through the catalyst column.

4. The process of claim I wherein the effluent is recycled through the catalyst column at least once.

5. The process of claim 1 wherein the Michael donor and Michael acceptor are fed through the catalyst column so that the effluent is obtained in 5–60 minutes.

6. The process of claim 1 wherein the catalyst is anhydrous potassium carbonate.

7. The process of claim 1 wherein the Michael donor is a dialkyl malonate corresponding to the formula $CH_2(COOR)_2$ and the Michael acceptor is an alkyl acrylate corresponding to the formula $CH_2\!\!=\!\!CHCOOR$, in which formulas each R is independently selected from alkyl groups containing 1–30 carbons.

8. The process of claim 1 wherein the Michael donor is a dialkyl malonate corresponding to the formula $CH_2(COOR)_2$ and the Michael acceptor is a compound corresponding to the formula $CH_2\!\!=\!\![CH_2\!\!-\!\!CH(COOR")]_m\!\!-\!\!(CH_2)_n\!\!-\!\!COOR"$, in which formulas R and R" are independently selected from alkyl groups containing 1–30 carbons, m is zero or an integer of 1–10, and n is an integer of 1–4, with the proviso that m must be zero when n is one.

* * * * *